(12) United States Patent
Babb et al.

(10) Patent No.: US 8,519,172 B2
(45) Date of Patent: Aug. 27, 2013

(54) DECOLORIZATION OF POLYOLS

(75) Inventors: David A. Babb, Lake Jackson, TX (US); Matthias Schaefer, Terneuzen (NL)

(73) Assignee: Dow Global Technologies LLC, Midland, MI (US)

(*) Notice: Subject to any disclaimer, the term of this patent is extended or adjusted under 35 U.S.C. 154(b) by 0 days.

(21) Appl. No.: 13/513,078

(22) PCT Filed: Nov. 15, 2010

(86) PCT No.: PCT/US2010/056672
§ 371 (c)(1),
(2), (4) Date: May 31, 2012

(87) PCT Pub. No.: WO2011/068664
PCT Pub. Date: Jun. 9, 2011

(65) Prior Publication Data
US 2012/0238769 A1    Sep. 20, 2012

Related U.S. Application Data

(60) Provisional application No. 61/266,244, filed on Dec. 3, 2009.

(51) Int. Cl.
*C07C 51/43*    (2006.01)
(52) U.S. Cl.
USPC ............................................ 554/175; 554/213
(58) Field of Classification Search
USPC .................................................. 554/175, 213
See application file for complete search history.

(56) References Cited

U.S. PATENT DOCUMENTS

| 4,633,021 A | 12/1986 | Hanes |
| 4,731,486 A | 3/1988 | Abatjoglou et al. |
| 4,942,228 A * | 7/1990 | Gibson ......................... 536/119 |
| 7,615,658 B2 | 11/2009 | Lysenko et al. |
| 2006/0193802 A1 | 8/2006 | Lysenko et al. |

FOREIGN PATENT DOCUMENTS

| DE | 4304468 | 8/1994 |
| DE | 4304468 A1 * | 8/1994 |
| EP | 2019088 A2 * | 1/2009 |
| EP | 2029088 | 1/2009 |
| EP | 2204358 | 7/2010 |
| GB | 2061941 | 5/1981 |
| WO | 2004096882 | 11/2004 |
| WO | 2004096883 | 11/2004 |
| WO | 2009117630 | 9/2009 |

OTHER PUBLICATIONS

International Search Report and Written Opinion mailed Feb. 22, 2011 for PCT App. No. PCT/US2010/056672.

* cited by examiner

*Primary Examiner* — Deborah D Carr
(74) *Attorney, Agent, or Firm* — Whyte Hirschboeck Dudek S.C.

(57) ABSTRACT

Natural oil-based polyols that are high in color, e.g., >40 APHA, are decolorized when exposed to high frequency visible light and/or low frequency UV light, with or without the combination of heat and/or air exposure.

9 Claims, 1 Drawing Sheet

DECOLORIZATION OF POLYOLS

FIELD OF THE INVENTION

This invention relates to polyols. In one aspect the invention relates to polyols prepared from hydroxymethylated fatty acid methyl esters while in another aspect, the invention relates to the de-colorization of such polyols.

BACKGROUND OF THE INVENTION

Natural oil-based polyols (NOBP) are typically polyester or hybrid polyether/polyester polyols, and are derived at least partially from plant-sourced triglycerides (oils). These oils consist of mostly $C_{18}$ fatty acids containing from 0 to 3 sites of unsaturation each. In order to manufacture polyols, the fatty acids are isolated away from the glycerin core and are functionalized to provide an alcohol/methyl ester monomer in a process which has been well-described, e.g., U.S. Pat. No. 7,615,658. The hydroxymethyl functional groups are added via a hydroformylation reaction followed by hydrogenation which reduces aldehydes to alcohols and unsaturated carbon bonds to saturated hydrocarbons.

In the final step of the natural oil polyol production, the hydroxymethylated methyl esters are reacted with an initiator to build the finished polyol product. This transesterification reaction is run in the presence of a Lewis acid catalyst, e.g., stannous octanoate, which serves as the catalyst. During polymerization organic chromophores are formed in the polyol. While these types of reactions are rare due to the dilute nature of the precursors, they can produce undesirable color in the polyol.

APHA color is a color standard named for the American Public Health Association and defined by ASTM D1209. One color specification for polyol products is 40 APHA with some end-use applications requiring even lower color (e.g., less than (<) 20 APHA). Some natural oil-based polyols have a color of greater than (>) 40 APHA upon completion of the polymerization step.

SUMMARY OF THE INVENTION

Natural oil-based polyols that are high in color, e.g., >40 APHA, can be decolorized when exposed to high frequency visible light and/or low frequency UV light, with or without the combination of heat and/or air exposure. The decolorization can be carried out effectively at room temperature under nitrogen, but can also be accelerated by heating the polyol during light exposure, and can especially be accelerated by exposure to air or oxygen while heating and exposing to light. Typically the wavelength of light is in the range of 250 to 550 nanometers (nm).

In one embodiment the invention is a process for decolorizing a natural oil polyol, the process comprising the step of exposing the polyol to actinic radiation of a wavelength of 250 to 550 nanometers. In one embodiment the polyol is contacted with oxygen at the same time it is exposed to the actinic radiation. In one embodiment the polyol is exposed to the actinic radiation at a temperature between ambient and 120° C. In one embodiment the polyol is simultaneously exposed to the actinic radiation and oxygen at a temperature between ambient and 120° C. In one embodiment the polyol is derived from a vegetable oil.

DESCRIPTION OF THE PREFERRED EMBODIMENT

Definitions

Figure 1A:
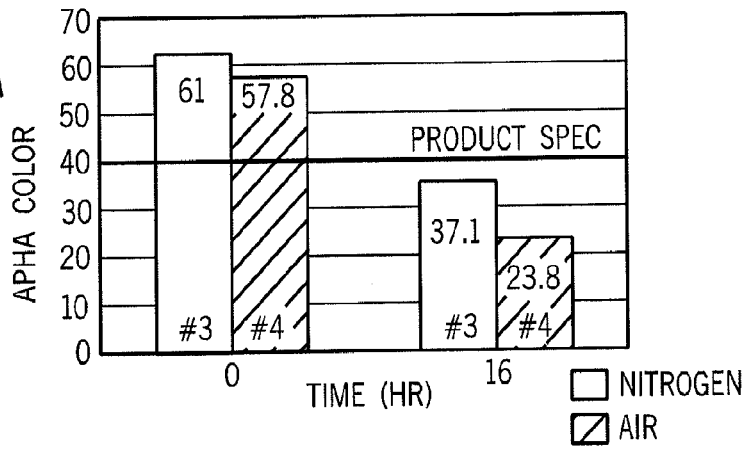
FIG. 1A is a bar graph reporting the APHA color measurement results of polyol decolorization under oxygen and nitrogen sweeps.

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the light wavelength and various process parameters.

Natural Oil-Based Polyols

Natural oil-based polyols (NOBP) are polyols based on or derived from renewable feedstock resources such as natural and/or genetically modified plant vegetable seed oils and/or animal source fats. Such oils and/or fats are generally comprised of triglycerides, that is, fatty acids linked together with glycerol. Preferred are vegetable oils that have at least about 70 percent unsaturated fatty acids in the triglyceride. Preferably the natural product contains at least 85 percent by weight unsaturated fatty acids. Examples of preferred vegetable oils include, but are not limited to, those from castor, soybean, olive, peanut, rapeseed, corn, sesame, cotton, canola, safflower, linseed, palm, grapeseed, black caraway, pumpkin kernel, borage seed, wood germ, apricot kernel, pistachio, almond, macadamia nut, avocado, sea buckthorn, hemp, hazelnut, evening primrose, wild rose, thistle, walnut, sunflower, jatropha seed oils, or a combination of two or more of these oils. Examples of animal products include lard, beef tallow, fish oils and mixtures of two or more of these products. Additionally, oils obtained from organisms such as algae may also be used. Combination of vegetable, algae, and animal based oils/fats may also be used.

The modified natural oil derived polyols may be obtained by a multistep process in which the animal or vegetable oils/fats are subjected to transesterification and the constituent fatty acids recovered. This step is followed by hydroformylating carbon-carbon double bonds in the constituent fatty acids to form hydroxymethyl groups. Suitable hydroformylation methods are described in U.S. Pat. Nos. 4,731,486 and 4,633,021, for example, and in U.S. Published Patent Application 2006/0193802. The hydroxymethylated fatty acids are "monomers" which form one of the building blocks for the natural oil based polyol. The monomers may be a single kind of hydroxymethylated fatty acid and/or hydroxymethylated fatty acid methyl ester, such as hydroxymethylated oleic acid or methylester thereof, hydroxymethylated linoleic acid or methylester thereof, hydroxymethylated linolenic acid or methylester thereof, α- and γ-linolenic acid or methyl ester thereof, myristoleic acid or methyl ester thereof, palmitoleic acid or methyl ester thereof, oleic acid or methyl ester thereof, vaccenic acid or methyl ester thereof, petroselinic acid or methyl ester thereof, gadoleic acid or methyl ester thereof, erucic acid or methyl ester thereof, nervonic acid or methyl ester thereof, stearidonic acid or methyl ester thereof, arachidonic acid or methyl ester thereof, timnodonic acid or methyl ester thereof, clupanodonic acid or methyl ester thereof, cervonic acid or methyl ester thereof, or hydroxymethylated ricinoleic acid or methylester thereof. In one embodiment the monomer is hydroformylated/hydrogenated methyloelate. Alternatively, the monomer may be the product of hydroformylating and hydrogenating the mixture of fatty acids recovered from transesterification process of the animal or vegetable oils/fats. In one embodiment the monomer is hydroformylated soy bean fatty acids. In another embodiment the monomer is hydroformylated castor bean fatty acids. In another embodiment the monomer may be a mixture of selected hydroxymethylated fatty acids or methylesters thereof.

The polyol is formed by the reaction of the monomer with an appropriate initiator compound to form a polyester or polyether/polyester polyol. Such a multistep process is commonly known in the art, and is described, for example, in PCT publication Nos. WO 2004/096882 and 2004/096883. The multistep process can result in the production of a polyol with both hydrophobic and hydrophilic moieties, which results in enhanced miscibility with both water and conventional petroleum-based polyols.

The initiator for use in the multistep process for the production of the natural oil derived polyols may be any initiator used in the production of conventional petroleum-based polyols. Preferably the initiator is selected from the group consisting of neopentylglycol; 1,2-propylene glycol; trimethylolpropane; pentaerythritol; sorbitol; sucrose; glycerol; aminoalcohols such as ethanolamine, diethanolamine, and triethanolamine; alkanediols such as 1,6-hexanediol, 1,4-butanediol; 1,4-cyclohexane diol; 1,3-cyclohexanedimethanol, 1,4-cyclohexanedimethanol, 2,5-hexanediol; ethylene glycol; diethylene glycol, triethylene glycol; bis-3-aminopropyl methylamine; ethylene diamine; diethylene triamine; 9(1)-hydroxymethyloctadecanol, 1,4-bishydroxymethylcyclohexane; 8,8-bis(hydroxymethyl)tricyclo[$5,2,1,0^{2,6}$]decene; Dimerol alcohol (36 carbon diol available from Henkel Corporation); hydrogenated bisphenol; 9,9(10,10)-bishydroxymethyloctadecanol; 1,2,6-hexanetriol and combination thereof. Preferably the initiator is selected from the group consisting of glycerol; ethylene glycol; 1,2-propylene glycol; trimethylolpropane; ethylene diamine; pentaerythritol; diethylene triamine; sorbitol; sucrose; or any of the aforementioned in which at least one of the alcohol or amine groups present has been reacted with ethylene oxide, propylene oxide or mixture thereof; and combinations thereof. Preferably, the initiator is glycerol, trimethylolpropane, pentaerythritol, sucrose, sorbitol, and/or mixture thereof. Other initiators include other linear and cyclic compounds containing an amine. Exemplary polyamine initiators include ethylene diamine, neopentyldiamine, 1,6-diaminohexane; bisaminomethyltricyclodecane; bisaminocyclohexane; diethylene triamine; bis-3-aminopropyl methylamine; triethylene tetramine various isomers of toluene diamine; diphenylmethane diamine; N-methyl-1,2-ethanediamine, N-methyl-1,3-propanediamine, N,N-dimethyl-1,3-diaminopropane, N,N-dimethylethanolamine, 3,3'-diamino-N-methyldipropylamine, N,N-dimethyldipropylenetriamine and aminopropyl-imidazole.

In one embodiment the initiators are alkoxylated with ethylene oxide, propylene oxide, or a mixture of ethylene oxide and at least one other alkylene oxide to give an alkoxylated initiator with a number average molecular weight (Mn) between 200 and 6000, preferably between 500 and 5000. In one embodiment the initiator has a Mn of 550, in another embodiment the Mn is 625, and in yet another embodiment the initiator has a Mn of 4600.

In one embodiment at least one initiator is a polyether initiator having an equivalent weight of at least 400 or an average at least 9.5 ether groups per active hydrogen group, and such initiators are described in WO 2009/117630.

The ether groups of the polyether initiator may be in poly(alkylene oxide) chains, such as in polypropylene oxide) or poly(ethylene oxide) or a combination thereof. In one embodiment the ether groups may be in a diblock structure of polypropylene oxide) capped with poly(ethylene oxide).

In one embodiment, a NOBP is made with an initiator or combination of initiators having an average equivalent weight of between 50 and 3000 per active hydrogen group. The average equivalent weight can be from a lower limit of 50, 75, 100, 125, 150, 200, 250, 300, 350, 400, 450, 480, 500, 550, 600, 650, 700, 800, 900, 1000, 1200, or 1300 to an upper limit of 1500, 1750, 2000, 2250, 2500, 2750, or 3000 per active hydrogen group.

Thus, in this embodiment, at least two of the natural oil based monomers are separated by a molecular structure having an Mn of between 100 Daltons and 6000 Daltons. The Mn can be from a lower limit of 100, 150, 200, 250 or 300 Daltons to an upper limit of 3000, 3500, 4000, 4500, 5000, 5500, or 6000 Daltons.

To form the polyether initiator, the active hydrogen groups may be reacted with at least one alkylene oxide, such ethylene oxide or propylene oxide or a combination thereof; or a block of propylene oxide followed by a block of ethylene oxide, to form a polyether polyol by means within the skill in the art. The polyether initiator may be used as an initiator for reaction with at least one natural oil based monomer. Alternatively the initiator is reacted by means within the skill in the art to convert one or more hydroxyl groups to alternative active hydrogen groups, such as is propylene oxide.

Thus, in one embodiment the natural oil based polyol may comprise at least two natural oil moieties separated by a molecular structure having at least 19 ether groups or having an equivalent weight of at least 400, preferably both. When the polyether initiator has more than 2 active hydrogen groups reactive with the natural oil or derivative thereof, each natural oil moiety is separated from another by an average of at least 19 ether groups or a structure of molecular weight of at least 400, preferably both.

The functionality of the resulting natural oil based polyols is above 1.5 and generally not higher than 6. In one embodiment the functionality is below 4. The hydroxyl number of the of the natural oil based polyols may be below 300 mg KOH/g, preferably between 50 and 300, preferably between 60 and 200. In at least one embodiment, the hydroxyl number is below 100.

Decolorization Process

In one embodiment the invention is contacting a polyol, especially a polyol prepared by a multistep process including first subjecting a vegetable oil to transesterification with methanol to form constituent unsaturated fatty acid methyl esters and then hydroformylating the carbon-carbon double bonds in the constituent fatty acid esters followed by hydrogenation to form hydroxymethyl groups, with actinic radiation with a wavelength in the range of 250 to 550, preferably 300 to 500 and more preferably 350 to 450, nanometers. This range of actinic radiation includes high frequency visible light and low frequency ultraviolet (UV) light. The source of the actinic radiation can vary along with its strength (intensity), configuration (e.g., fluorescent lamp, light tube, etc.) and placement relative to the polyol.

The contacting is performed in any convenient manner. In one embodiment the polyol is held in vessel or other container at least a part of which will allow the actinic radiation to pass from a source outside the vessel to the polyol within the container. In another embodiment the radiation source is located within the container. In another embodiment the radiation source is located outside, typically above, an opening in the container. While in the container the polyol can be either quiescent or agitated (by any means, e.g., stirring, sparging with a gas, etc.). In one embodiment the polyol passes through a pipe equipped with an actinic radiation source, e.g., a "light pipe". The flow through the pipe can be either laminar or turbulent. The length of time to which the polyol is exposed to the radiation is a function of a number of factors including but not limited to the intensity of the radiation source, the distance between the radiation source and the polyol, the degree to which the radiation can pass through the vessel and penetrate into the polyol, the length of the pipe, and similar factors.

In one embodiment the polyol is contacted with actinic radiation and heat. The temperature at which the polyol and actinic radiation are contacted can vary, but typically it is between ambient or room temperature (e.g., 23° C.) and 120° C. The presence of heat during the contacting accelerates the decolorization process and as such, the use of heat is preferred. Typically, the polyol is heated to a temperature of at least 40, preferably at least 50 and more preferably to a range of 50 to 90, ° C. The heat can be imparted to the polyol by any convenient means.

In one embodiment the polyol is contacted with actinic radiation and oxygen. Any source of oxygen can be used, but typically the oxygen is supplied as neat oxygen, air or enriched air. The oxygen can be brought into contact with the polyol in any convenient manner, e.g., as a blanket (pressurized or ambient) over an exposed top surface of polyol held in a vessel (open or closed), sparged through the polyol held in a vessel, injected into a pipe through which the polyol is passing, etc. The presence of oxygen during the contacting accelerates the decolorization process and as such, the use of oxygen is preferred. The oxygen can be present at ambient, e.g., atmospheric, pressure, or at a super-atmospheric pressure.

In one embodiment the polyol is contacted simultaneously with the actinic radiation, heat and oxygen.

The polyol is contacted with the actinic radiation, with or without heat and/or oxygen, for a period of time sufficient to reduce the APHA color. The color reduction will vary with the polyol and the conditions of the decolorization process and in one embodiment, the color reduction is from an APHA color value above 40 to an APHA color value of 40 or less, preferably 20 or less. In one embodiment the decolorization process is conducted at part of a polyol production process, e.g., after the polymerization step in which the polyol is formed and before an antioxidant is added, typically before packaging and storage and/or use as a reactant in a polyurethane process.

Many natural oil-based polyols can be effectively decolorized to a color less than 40 APHA after the final polymerization step by exposure to light in the range from 250 nm to 550 nm after air exposure. The process is most effective when the polyols have been prepared carefully to minimize color during polyol formation to reduce the initial polyol color. The process is effective under aerobic conditions, and is usually accelerated in the presence of oxygen and/or heat. Moreover, simultaneous decolorization of NOBP and deactivation of residual catalyst that remains in the polyol at the end of the polymerization reaction is also possible, preferably in the presence of oxygen.

The following examples are illustrative of certain embodiments of the present invention. All parts and percentages are based on weight except as otherwise indicated.

SPECIFIC EMBODIMENTS

Preparation of Polyols

Natural oil monomer (NOM) is obtained from a commercial manufacturing campaign using the process described in U.S. Pat. No. 7,615,658, and it is used exclusively for all the following reported examples.

The following preparative method illustrates the means of polyol preparation, and it is not intended to limit the sequence of process steps or conditions for accomplishing the polymerization. Those skilled in the art will recognize that the polymerization step may be modified in other ways to make the procedure convenient to individual circumstances. In one example of a polyol preparative method, a two liter, 3-necked round bottom flask is operated without vacuum to rigorously exclude air from the experiment. Only nitrogen purging is used, the purge stream being passed through a condenser working at room temperature followed by a cold trap. A heating mantle and temperature controller are placed on the flask. The flask is charged with initiator, natural oil monomer and DABCO T9 (a stannous octanate catalyst available from Air Products & Chemicals, Inc.). The catalyst is added after holding the reactor content between 70° C. and 90° C. for at least 30 minutes to strip off residual moisture. The content of the flasks is then heated to polymerization temperature, typically 195° C. The point in time at which the content of the flask reached polymerization temperature is defined as the starting point of the reaction (t=0). The reaction mixture is then held at polymerization temperature for approximately 5 hours. After that the mixture is allowed to cool to about 90° C. for optional addition of approximately 400 ppm of water.

Polyol Decolorization

Ultra-violet exposure in lab experiments is provided by:
1) A 26 watt fluorescent UVA/UVB light source (Repti-Sun 5.0 compact fluorescent UV-B lamp; Zoo Med Laboratories, Inc., Item# FS-C5).
2) UV light centered at 254 nm is provided by a Model XX-15G Germicidal lamp from Spectronics Corporation (Westbury, N.Y.) with dual 15-Watt mercury discharge lamps. This lamp is also capable of light emissions centered at 302 nm and 365 nm, and these settings are used exclusively for Experiment #5.

3) UV/Visible light centered at 365 nm is provided by a Model CX-20 UV viewing cabinet with a single 8-watt Mercury tube with filter from Spectronics Corporation (Westbury, N.Y.).

UV-Visible spectra are measured with a Shimadzu Model UV-3600 UV-Vis spectrometer. In some decolorization studies, samples of polyols are removed directly from the reaction vessel and measured for APHA color immediately. In other decolorization studies, polyols are transferred to 20 ml glass vials and exposed to UVA/UVB light in an oven at temperatures as specified by the experimental conditions (see FIG. 2 for the experimental set-up). The samples are taken out of the oven in certain time intervals to measure APHA color.

Example 1

Observation of the Decolorization of NOBP

NOM (1029.2 g; 3.13 mole) and ethoxylated glycerin initiator having a number average molecular weight of 625 (470.8 g, 0.766 mole) are combined in a monomer/initiator mole ratio of 4.1. The mixture is heated to 185° C. with stirring and nitrogen stripping in the apparatus described in FIG. 1, and stannous octoate (0.75 g) is then added to the mixture. The polyol is stirred at reaction temperature at 185° C. for 5 hours, then cooled to room temperature, after which the viscosity of the mixture is measured and found to be 1650 cPs, indicating that the polyol had not reached full conversion (the specified viscosity range is 1850 cPs to 2250 cPs). A sample (#1) is removed from the reactor through the bottom drain and the color is measured to be 44.9 APHA. The polyol is heated again to 185° C. with nitrogen stripping for 2 additional hours, then cooled to 50° C. under a continuous nitrogen strip, at which time the polyol is again sampled. The sample (#2) is dispensed in air through the reactor bottom drain valve at 50° C. The color is measured and found to be 48 APHA, with a polyol viscosity of 2069 cPs, indicating that the polyol has reached >97% conversion. At the same time sample #1 is measured again for color, and is found to be 32.7 APHA, after sitting at room temperature in the laboratory for 6 hours. The remainder of the polyol produced from this reaction is held under constant nitrogen purge at room temperature in a laboratory fume hood in the Pyrex™ reactor in which it is formed.

Two days after the completion of the reaction, the final polyol (sample #3) is very carefully collected at room temperature via syringe through a septum under stringent nitrogen pad, and is dispensed into a color-measurement polystyrene cuvette which is capped with a rubber septum and vigorously swept with nitrogen to prevent oxygen exposure to the polyol before color measurement. A second sample (#4) is also collected carefully under nitrogen, but is instead dispensed into a cuvette which is vigorously swept with air. Sample #3 has an initial APHA color value of 61.05 (61.0; 61.1) while the sample dispensed in air (#4) has an initial color value of 57.8 (57.7; 57.9). These two samples are allowed to sit on the laboratory bench overnight with the laboratory lights on, sweeping the samples (not sparging with gas into the liquid, but only sweeping across the top of the liquid) with nitrogen or air, respectively, for a total of 16 hours after which the color is measured again. The sample held under nitrogen has dropped to 37.1 APHA (37.2; 37.1; 36.9) while the sample held under a sweep of air has dropped to 23.8 APHA (23.8; 23.8; 23.7). This experiment indicates that exposure to laboratory light in the absence of air had a significant impact on the color of the polyol but that exposure to air accelerates the effect.

Figure 1B:
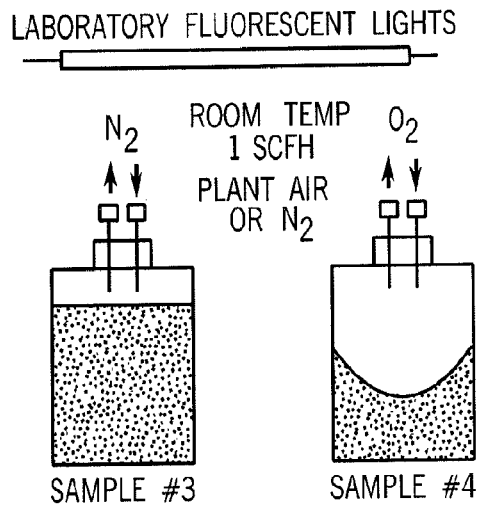
FIG. 1B is a schematic of the experimental set-up used to generate the results reported in FIG. 1A.

An additional interesting observation is made during this example. By observing the cuvette which is swept with air it is possible to see a line of color transition, reproduced in FIG. 1A below, which migrates downward in the air-swept sample over the course of the first 2 hours of exposure. The experimental apparatus for this study is illustrated in FIG. 1 B. In normal laboratory lighting, decolorization occurs faster in the presence of air than in nitrogen.

Example 2

Simultaneous Decolorization of NOBP and Deactivation of Residual Catalyst

The polyol which is produced in Example #1 and stored under nitrogen in the reaction flask remains at the original APHA color value of 60 APHA throughout the previous experiments, and for the period of 1 week under laboratory lights leading up to this example. This observation is relevant to Example 2.

A sample of the reactor contents is removed through the bottom drain valve while carefully sweeping the UV cuvette with nitrogen. The APHA color is measured immediately and found to be 60.1 APHA. The reactor is heated slowly to 55° C., and the nitrogen inlet tube is switched to a supply of air. Air is then sparged through the reactor at a temperature of 55° C. for one hour, at a rate of 1 standard cubic foot per minute (scfm) with no other light supplied to the reactor other than the fluorescent lamps (GE CoolWhite™) which are in the fume hood where it is located. After a period of 1 hour the polyol is cooled to room temperature and again sampled through the bottom drain port as before. The APHA color is measured immediately again and is found to be 25.4 APHA.

The resulting polyol sample is analyzed for reactivity by Brookfield Viscosity Test (BVT). The sample is determined to reach a polyol viscosity of only 40,000 cPs after 2 hours which qualifies as deactivated polyol. The results of this experiment are outlined in FIG. 2.

Example 3

Effects of Different Process Variables on Decolorization

For all of the runs in this example, a sample of high colored polyol from the Example 1 (55 APHA color) is dispensed from a 2 gallon HDPE bottle stored on a laboratory shelf into soda lime glass APHA color cuvettes.

Polyol is dispensed into a cuvette and is left open inside a fume hood with the lights turned off. The color is measured at time 0, then at 1, 5 and 10 minutes. The procedure is repeated but after the time 0 color measurement, the sample is opened and placed under a hand-held UV imaging lamp with a low light flux exposure at 365 nm. The sample is again measured for APHA color at 1, 5 and 10 minutes. This procedure is repeated again with exposures at 302 nm and 254 nm. The results are presented in Table 2.

TABLE 2

Exposure of NOBP to Different Wavelengths of UV Light

| Time (min) | Baseline | 254 nm | 306 nm | 365 nm |
|---|---|---|---|---|
| 0 | 40.33 | 39.2 | 38.9 | 39.1 |
| 1 | 40.36 | 39.4 | 38.5 | 35.8 |
| 5 | 39.05 | 36.12 | 39.07 | 38.9 |
| 10 | 38.83 | 37.95 | 38.92 | 37.9 |

This experiment demonstrates that the effect of low flux light exposure is minimal over a period of a few minutes at room temperature, at wavelengths that span the UV spectrum of unsaturated carbon bonds.

Another sample of high colored polyol (55 APHA color) is dispensed from the 2-gallon HDPE bottle into four (4) soda lime glass APHA color cuvettes. Sample #1 is measured for the starting APHA color value, then is immediately closed and sealed in multiple layers of aluminum foil to exclude light, and is placed in a freezer at 20° C., for the "cold, dark, sealed" sample. Sample #2 is measured for color, then also closed, wrapped in aluminum foil, and placed under a dark box on the laboratory bench for the "dark, sealed" sample. A third sample is measured, then left open to the air and placed under a dark box for the "dark, open" sample. Next, a 4$^{th}$ sample is dispensed into a cuvette, measured for the initial APHA color value, then placed open in a fume hood (air flow turned off) under a hand-held UV imaging lamp at an exposure wavelength of 365 nm, for a period of 8 hours. After a period of 8 hours all four samples are measured again for APHA color. The entire experiment is repeated again, this time the 4th sample is exposed under 302 nm light for 8 hours. The experiment for the 302 nm light is altered by allowing the air flow through the fume hood to remain flowing during the experiment. The experiment is then repeated for a third time, with the 4$^{th}$ sample being exposed under 254 nm light.

TABLE 3

Influence of Air and Light Exposure on the Decrease of APHA Color

| Time (h) | Cold Dark Sealed | Dark Sealed | Dark Open | 365 nm Open |
|---|---|---|---|---|
| 0 | 51.6 | 52.3 | 52.0 | 52.8 |
| 8 | 52.6 | 53.8 | 51.7 | 41.1 |
|   |      |      |      | 302 nm Open |
| 0 | 51.7 | 52.5 | 52.5 | 52.7 |
| 8 | 53.1 | 54.6 | 54.6 | 31.3 |
|   |      |      |      | 254 nm Open |
| 0 | 55.8 | 57.4 | 54.4 | 54.4 |
| 8 | 65.8 | 58.0 | 59.2 | 41.3 |

The results of this example indicate that the greatest effect on decolorization of NOBP occurs with the combination of exposure to air and UV light at a wavelength of 302 nm. Results also indicate that over the 8 hour timeframe of the experiment, exposure to air in the absence of light at room temperature did not have an effect on decolorization.

Example 4

Exclusion of Oxygen

Samples are exposed to the UVA/UVB lamp at three different temperatures, for 5 different time periods each. Results clearly show that exposure to air improves the rate of decolorization but that decolorization can be performed without exposure to air.

A one-half gallon sample of a high-color batch of polyol from Example 1 is dispensed into a one-half gallon plastic screw-cap container. The open container is placed in the anti-chamber of a nitrogen glove box along with 24 APHA color measurement cuvette sample vials and cycled through an automatic high vacuum pad/depad process 4 times to remove residual dissolved oxygen in the polyol. The sample is then transported into the glove box and is allowed to sit open in the glove box overnight.

The next morning fifteen sample vials are prepared with the label "N$_2$/dark" written on the vial cap, filled with polyol, and are immediately wrapped with aluminum foil to keep them in the dark: An additional fifteen vials are prepared with the label "N$_2$/light" written on the vial cap, filled with polyol and are left unwrapped. All the samples are placed in an opaque polypropylene bucket and are transported out of the nitrogen glove box along with the closed one-half gallon container of polyol.

The polyol container is then fitted with a sparge tube connected to an air line, and the polyol is sparged with air for 10 minutes at a rate of 1 scfm in order to saturate the sample with air. The polyol is then dispensed into fifteen sample vials which are prepared with the label "Air/dark" written on the vial cap, and are immediately wrapped with aluminum foil. The polyol is then dispensed into fifteen additional vials which are prepared with the label "Air/light" written on the vial cap, and are left unwrapped. All samples are placed inside the plastic bucket.

The fluorescent UVA/UVB light source is hung inside the oven through a thermometer hole in the top of the oven. Five samples of each type (N$_2$/dark; N$_2$/light; Air/dark; Air/light) were placed in a sample holder and are placed inside a temperature controlled oven at 30° C. The samples are allowed 15 minutes inside the oven to reach the experimental temperature, and then the light is turned on. One sample of each type is removed from the oven and is measured for APHA color after 30, 60, 90, 120 and 180 minutes. The experiment is repeated at 40° C. and at 50° C. The results are reported in Tables 4A, 4B and 4C.

TABLE 4A

APHA Color Measurements at 30° C.

| | Initial APHA = 50.05 | | | | Initial APHA = 72 | |
|---|---|---|---|---|---|---|
| Time (min) | Air Light | Air Dark | N2 Light | N2 Dark | Air Light | N2 Light |
| 30 | 42.14 | 47.96 | 42.96 | 46.33 | 64.62 | 69.41 |
| 60 | 36.56 | 47.00 | 39.34 | 46.51 | 57.56 | 66.74 |
| 90 | 35.40 | 46.81 | 35.72 | 46.25 | 56.28 | 63.44 |
| 120 | 33.20 | 46.82 | 35.37 | 46.35 | 52.73 | 60.99 |
| 180 | 33.56 | 46.56 | 32.59 | 46.35 | 55.29 | 61.43 |

TABLE 4B

APHA Color Measurements at 40° C.

| | Initial APHA = 50.05 | | | | Initial APHA = 72 | |
|---|---|---|---|---|---|---|
| Time (min) | Air Light | Air Dark | N2 Light | N2 Dark | Air Light | N2 Light |
| 30 | 43.19 | 46.97 | 41.26 | 45.81 | 63.03 | 69.86 |
| 60 | 40.19 | 46.15 | 34.74 | 44.49 | 58.61 | 66.85 |

TABLE 4B-continued

APHA Color Measurements at 40° C.

| | Initial APHA = 50.05 | | | | Initial APHA = 72 | |
|---|---|---|---|---|---|---|
| Time (min) | Air Light | Air Dark | N2 Light | N2 Dark | Air Light | N2 Light |
| 90 | 36.64 | 45.77 | 31.53 | 45.46 | 52.99 | 63.19 |
| 120 | 32.87 | 45.34 | 32.53 | 44.88 | 49.43 | 62.86 |
| 180 | 33.40 | 45.45 | 31.15 | 44.88 | 51.79 | 59.32 |

TABLE 4C

APHA Color Measurements at 50° C.

| | Initial APHA = 50.05 | | | | Initial APHA = 72 | |
|---|---|---|---|---|---|---|
| Time (min) | Air Light | Air Dark | N2 Light | N2 Dark | Air Light | N2 Light |
| 30 | 40.62 | 44.91 | 36.44 | 44.21 | 60.89 | 69.72 |
| 60 | 36.07 | 44.66 | 34.95 | 44.86 | 52.02 | 65.29 |
| 90 | 34.33 | 44.38 | 31.83 | 43.71 | 52.03 | 61.32 |
| 120 | 30.47 | 44.00 | 32.14 | 43.84 | 48.33 | 61.42 |
| 180 | 30.00 | 44.17 | 31.66 | 43.66 | 44.51 | 59.81 |

Example 4 demonstrates that UV exposure accelerates the rate of decolorization of the natural oil-based polyol. The data demonstrates that decolorization at elevated temperatures with exposure to air and UV light is faster than exposure to air in the dark. The heating of polyol in nitrogen or air in the dark had little effect on decreasing the color of the polyol, while exposing the polyol to UV light in air or nitrogen at any temperature had a significant impact on the color of the polyol after 3 hours of treatment.

Example 5

Decolorization of a NOBP

Natural oil monomer (NOM) (1009.2 g; 2.96 mole) and UNOXOL™ Diol initiator (an approximate 1:1 mixture of (cis, trans) 1,3-cyclohexanedimethanol and (cis, trans) 1,4-cyclohexanedimethanol available from The Dow Chemical Company) are combined in a monomer/initiator mole ratio of 2:1. The mixture is heated and held between 70° C. and 90° C. for 30 minutes with stirring and nitrogen stripping in the apparatus described in FIG. 1. Stannous octoate (0.85 g) is then added to the mixture. The mixture is heated to 195° C. with stirring and nitrogen stripping in the apparatus described in FIG. 1. The polyol is stirred at reaction temperature at 195° C. for 4.5 hours, cooled to room temperature, after which the viscosity of the mixture is measured and found to be 2200 cPs, which is within the specified viscosity range of the finished polyol. The polyol is then dispensed in air through the reactor bottom drain valve and stored in a HDPE plastic container.

Figure 2:
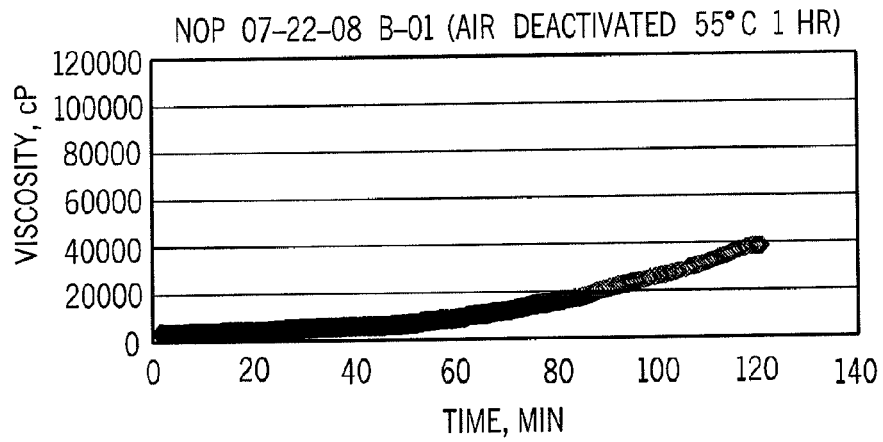
FIG. 2 is a line graph of concurrent decolorization and catalyst deactivation of a polyol treated with light and air at 55° C.

Eight days later a sample of the polyol is dispensed from the HDPE plastic container into an APHA color measurement sample vial. The fluorescent UVA/UVB light source is hung inside the oven through the thermometer hole in the top of the oven and turned on. The oven temperature increases to 31° C. due to the presence of the lamp. The sample is placed in a sample holder inside the oven as shown in FIG. 2. In certain time intervals the sample is removed from the oven, the APHA color is measured immediately, and the sample returned to the oven. Duration of light exposure and APHA color results are reported in Table 5.

TABLE 5

APHA Color as a Function of Duration of Light Exposure

| Time (min) | APHA Color |
|---|---|
| 0 | 87 |
| 35 | 84 |
| 65 | 81 |
| 95 | 77 |
| 130 | 74 |
| 160 | 70 |
| 215 | 66 |
| 275 | 62 |
| 330 | 60 |
| 395 | 60 |
| 455 | 57 |
| 530 | 52 |
| 590 | 50 |

Although the invention has been described with certain detail through the preceding specific embodiments, this detail is for the primary purpose of illustration. Many variations and modifications can be made by one skilled in the art without departing from the spirit and scope of the invention as described in the following claims.

What is claimed is:

1. A process for decolorizing a natural oil-based polyol, the process comprising the step of exposing the polyol to actinic radiation of a wavelength of 250 to 550 nanometers.

2. The process of claim 1 in which the polyol is exposed to the actinic radiation at a temperature between ambient and 120° C.

3. The process of claim 2 in which the polyol is simultaneously contacted with an oxygen source.

4. The process of claim 1 in which the polyol is derived from a vegetable oil.

5. The process of claim 4 in which the vegetable oil is subjected to transesterification followed by hydroformylation and then hydrogenation to form hydroxymethylated fatty acid methyl esters.

6. The process of claim 5 in which the hydroxymethylated fatty acid methyl esters are polymerized to form the polyol.

7. The process of claim 6 in which the hydroxymethylated fatty acid methyl esters are catalytically polymerized.

8. The process of claim 7 in which the catalyst is stannous octoate.

9. The process of claim 8 in which residual polymerization catalyst is deactivated simultaneously with the decolorization of the polyol.

* * * * *